United States Patent
Alvarez et al.

(10) Patent No.: US 6,867,172 B2
(45) Date of Patent: Mar. 15, 2005

(54) METHODS OF INHIBITING THE ADHERENCE OF LENSES TO THEIR PACKAGING

(75) Inventors: Nayiby Alvarez, Jacksonville, FL (US); Frank Molock, Orange Park, FL (US); Azaam Alli, Jacksonville, FL (US); James D. Ford, Orange Park, FL (US); Shivkumar Mahadevan, Starke, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 10/237,431

(22) Filed: Sep. 9, 2002

(65) Prior Publication Data

US 2003/0130144 A1 Jul. 10, 2003

Related U.S. Application Data

(63) Continuation-in-part of application No. 09/731,553, filed on Dec. 7, 2000, now Pat. No. 6,531,432.

(51) Int. Cl.[7] ................................................. C11D 3/22
(52) U.S. Cl. ..................... 510/112; 510/421; 510/470; 134/901
(58) Field of Search ............................... 510/112, 421, 510/470; 134/901

(56) References Cited

U.S. PATENT DOCUMENTS

| | | |
|---|---|---|
| 3,882,038 A | 5/1975 | Krezanoski et al. |
| 3,954,644 A | 5/1976 | Krezanoski et al. |
| 4,046,706 A | 9/1977 | Krezanoski et al. |
| 4,354,952 A | 10/1982 | Riedhammer et al. |
| 4,409,205 A | 10/1983 | Shively |
| 4,440,662 A | 4/1984 | Tsuzuki et al. |
| 4,613,380 A | 9/1986 | Chen |
| 4,814,109 A | 3/1989 | Wittpenn, Jr. et al. |
| 4,820,352 A | 4/1989 | Riedhammer et al. |
| 5,209,865 A | 5/1993 | Winterton et al. |
| 5,256,420 A | 10/1993 | Tsao et al. |
| 5,322,667 A | 6/1994 | Sherman |
| 5,785,767 A | 7/1998 | Kimura et al. |
| 5,849,222 A * | 12/1998 | Jen et al. ..................... 264/2.3 |
| 5,888,950 A | 3/1999 | Potini et al. |
| 6,037,328 A | 3/2000 | Hu et al. |
| 6,096,138 A | 8/2000 | Heiler |
| 6,184,190 B1 * | 2/2001 | D'Ambrogio et al. ...... 510/130 |
| 6,207,628 B1 * | 3/2001 | Soyer et al. ................ 510/112 |
| 2001/0014653 A1 | 8/2001 | Soyer et al. |

FOREIGN PATENT DOCUMENTS

| | | |
|---|---|---|
| EP | 0 439 429 A2 | 7/1991 |
| EP | 0 765 733 A2 | 4/1997 |
| WO | WO 98/55155 A2 | 12/1998 |
| WO | 98/55155 * | 12/1998 |

OTHER PUBLICATIONS

PCT International Search Report, dated Jan. 20, 2004, for PCT Int'l Appln. No. PCT/US03/27032.

* cited by examiner

*Primary Examiner*—Charles Boyer

(57) ABSTRACT

Methods of reducing the adherence of lenses to hydrophobic packing materials using compounds of Formula I are disclosed herein, where $R^1$–$R^{12}$, a, b, z, x, q, m, and n are defined herein

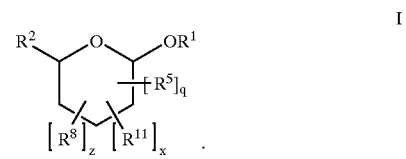

24 Claims, No Drawings

METHODS OF INHIBITING THE ADHERENCE OF LENSES TO THEIR PACKAGING

RELATED APPLICATIONS

This application is a Continuation-In-Part application of U.S. application Ser. No. 09/731,553, filed Dec. 7, 2000, now granted as U.S. Pat. No. 6,531,432.

This invention related to packaging solutions for use with contact lenses and methods for their use.

BACKGROUND

Contact lenses have been used commercially to improve vision since the 1950s. The first contact lenses were made of hard materials. Although these lenses are currently used, they are not suitable for all patients due to their poor initial comfort. Later developments in the field gave rise to soft contact lenses, based upon hydrogels, which are extremely popular today. These lenses have higher oxygen permeabilities and such are often more comfortable to wear than contact lenses made of hard materials. However, these new lenses are not without problems.

Contact lenses with high oxygen permeabilites are typically made of hydrophobic materials. The packaging for contact lenses are also made of hydrophobic materials. When one hydrophobic surface comes in contact with another, the surfaces stick to each other. The sticking of a contact lens to its packaging creates many problems. First the packaging is thicker and more rigid than the soft lenses contained therein. If a lens sticks to the packaging, when the user tries to remove the lens, the lens often tears and must be discarded. One solution to this problem is to place a hydrophilic additive such as a surfactant, into the lens packaging solution. However many surfactants that have been used to solve this problem do not prevent the sticking of contact lenses to their packaging. In addition, some surfactants do not completely dissolve in lens packaging solutions and have unfavorable interactions with the lens when they are stored over a period of time, Therefore there is a need for methods of inhibiting the adherence of contact lenses to their packaging. It is this need that is met by the following invention.

DETAILED DESCRIPTION OF THE INVENTION

This invention includes a method of inhibiting the adherence of soft lenses to hydrophobic packaging materials comprising, consisting essentially of, or consisting of storing the soft lenses in a packing solution comprising an effective amount of composition of Formula I

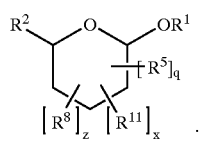

I wherein $R^1$ is $C_{1-6}$ alkyl;, $R^2$ is —$CH_2OH$, —$CH_2OR^3$, —$CH_2OC(O)R^4$
wherein $R^3$ is $C_{1-50}$alkyl, or $C_{1-51}$alkylene having at least one double bond, $R^4$ is hydrogen or $C_{1-12}$alkyl;

$R^5$ is —OH, or —$[(O—(CHR^7)_a)_n—OR^6]$
wherein $R^6$ is hydrogen $C_{1-50}$alkyl, or $C_{1-51}$alkylene having at least one double bond, $R^7$ is hydrogen or $C_{1-12}$alkyl;

$R^8$ is —OH or —$[(O—(CHR^{10})_b)_m—OR^9]$
wherein $R^9$ is hydrogen, $C_{1-50}$alkyl, or $C_{1-51}$alkylene having at least one double bond $R^{10}$ is hydrogen or $C_{1-12}$alkyl;

$R^{11}$ is —OH or —$OC(O)R^{12}$
wherein $R^{12}$ is $C_{1-50}$alkyl or $C_{1-51}$alkylene having at least one double bond;

a is 2–4;

b is 2–4;

x is 0–3;

q is 0–3;

z is 0–3
wherein the sum of x+q+z=3 m is an integer, from 1 to 200;

n is an integer from 1 to 200 wherein the sum of m+n=2 to 400
provided that if q is 3 $R^6$ is not ethyl;
provided that if z is 3 $R^9$ is not ethyl.

With respect to Formula I, all substituents are selected independent of one another. The term alkyl refers to straight or branched alkyl chains. Alkylene refers to a carbon radical having at least one point of unsaturation. The preferred values for the substituents are as follows:

$R^1$ is methyl, ethyl or propyl, $R^2$ is —$CH_2OC(O)R^4$, $R^3$ is $C_{10-18}$alkyl, $R^4$ is $C_{8-30}$alkyl, or $C_{10-30}$alkylene having at least one double bond, $R^5$ is —$[(O—(CHR^7)_a)_n—OR^6]$, $R^6$ is $C_{8-30}$alkyl, or $C_{10-30}$alkylene having at least one double bond, $R^7$ is hydrogen, $R^8$ is —$[(O—(CHR^{10})_b)_m—OR^9]$ $R^9$ is $C_{8-30}$alkyl, or $C_{10-30}$alkylene having at least one double bond, $R^{10}$ is hydrogen, $R^{11}$ is $OC(O)R^{12}$, $R^{12}$ is $C_{8-30}$alkyl or $C_{10-30}$alkylene having at least one double bond, a is 2–3, b is 2–3, x is 1, q is 1, z is 1, m is 60–140 n is 80–120, wherein the preferred sum of m+n is about 100–200.

Examples of suitable compositions of Formula I include but are not limited to CAS No. 119831-19-5, 223717-75-7, and 116057-48-8.

The most particularly preferred composition of Formula I is poly(oxy-1,2-ethandiyl) α-hydro-ω-hydroxy-, ether with methyl D-glucopyranoside 2,6-di-9Z-9-octadecenaoate, commercially known as Glucamate DOE 120.

The compositions of Formula I may be combined with any known active or carrier components useful for lens packing solutions. Suitable additional ingredients include but are not limited to antibacterial agents, anti-dryness agents, such a polyvinyl alcohol, polyvinyl pyrrolidone, and dextran, tonicity agents, and combinations thereof.

The packing solutions of the invention may be any water-based solution that is used for the storage of contact lenses. Typical solutions include, without limitation, saline solutions, other buffered solutions, and deionized water. The preferred aqueous solution is saline solution containing salts including, without limitation, sodium chloride, sodium borate, sodium phosphate, sodium hydrogenphosphate, sodium dihydrogenphosphate, or the corresponding potassium salts of the same. These ingredients are generally combined to form buffered solutions that include an acid and its conjugate base, so that addition of acids and bases cause only a relatively small change in pH. The buffered solutions may additionally include 2-(N-morpholino)ethanesulfonic acid (MES), sodium hydroxide, 2,2-bis(hydroxymethyl)-2, 2', 2"-nitrilotriethanol, n-tris(hydroxymethyl)methyl-2-aminoethanesulfonic acid, citric acid, sodium citrate, sodium carbonate, sodium bicarbonate, acetic acid, sodium acetate, ethylenediamine tetraacetic acid and the like and combinations thereof. Preferably, the solution is a borate buffered or phosphate buffered saline solution.

As used herein "soft lenses" refers to an ophthalmic devices that resides in or on the eye. These devices can provide optical correction or may be cosmetic. The term lens includes but is not limited to soft contact lenses, intraocular lenses, overlay lenses, ocular inserts, and optical inserts. The preferred lenses of the invention are soft contact lenses are made from silicone elastomers or hydrogels, which include but are not limited to silicone hydrogels, and fluorohydrogels. Soft contact lens formulations are disclosed in U.S. Pat. No. 5,710,302, WO 9421698, EP 406161, JP 2000016905, U.S. Pat. No. 5,998,498, U.S. patent application Ser. No. 09/532,943, U.S. Pat. No. 6,087,415, U.S. Pat. No. 5,760,100, U.S. Pat. No. 5,776,999, U.S. Pat. No. 5,789,461, U.S. Pat. No. 5,849,811, and U.S. Pat. No. 5,965,631. The foregoing references are hereby incorporated by reference in their entirety. The particularly preferred lenses of the inventions are etafilcon A, genfilcon A, lenefilcon A, and polymacon. The most preferred lenses include but are not limited to silicone hydrogels such as acquafilcon A, balafilcon A, lotrafilcon A, and silicone hydrogels as prepared in U.S. Pat. No. 5,998,498, U.S. patent application Ser. No. 09/532,943, a continuation-in-part of U.S. patent application Ser. No. 09/532,943, filed on Aug. 30, 2000, U.S. Pat. No. 6,087,415, U.S. Pat. No. 5,760,100, U.S. Pat. No. 5,776,999, U.S. Pat. No. 5,789,461, U.S. Pat. No. 5,849,811, and U.S. Pat. No. 5,965,631. These patents as well as all other patents disclosed in this application are hereby incorporated by reference in their entirety.

"Hydrophobic packaging materials," refer to substances that are used to prepare containers for manufacturing lenses prior to their use by an end user. These packaging materials are discarded by the user after the soft contact lens is placed in the eye of a user. Examples of hydrophobic packaging materials include but are not limited to polypropylene, polyethylene, nylons, olefin co-polymers, acrylics, rubbers, urethanes, polycarbonates, or fluorocarbons. The preferred materials are metallocenes polymers and co-polymers made of polypropylene, polyethylene, having a melt flow range of about 15 g/10 minutes to about 44 g/10 minutes as determined by ASTM D-1238. Containers made from hydrophobic packaging material may be in many forms. These containers may store a single lenses or many lenses. An example of a single lens storage unit is a blister package, such as the packages disclosed in the following publications, U.S. Pat. Nos. D435,966 S; 4,691,820; 5,467,868; 5,704,468; 5,823,327; 6,050,398, which are hereby incorporated by reference in their entirety. Examples of multiple lens storage units include the hydrophobic molds that are used to produce contact lenses as shown in U.S. Pat. No. 4,640,489 which is hereby incorporated in reference in its entirety.

The term "effective amount" refers to the percentage of weight of compositions of Formula I that will inhibit the adherence of lenses to hydrophobic packaging. The effective amount is about 0.01 weight percent to about 2.0 weight percent, preferably about 0.05 weight percent to about 1.50 weight percent, more preferably about 0.05 to about 0.1 weight percent.

In order to illustrate the invention the following examples are included. These examples do not limit the invention. They are meant only to suggest a method of practicing the invention. Those knowledgeable in contact lenses as well as other specialties may find other methods of practicing the invention. However, those methods are deemed to be within the scope of this invention.

EXAMPLES

The following abbreviations are used in the examples below:

| | |
|---|---|
| DMA | N,N-dimethylacrylamide |
| HEMA | 2-hydroxyethyl methacrylate |
| mPDMS | 800–1000 MW monomethacryloxypropyl terminated polydimethylsiloxane |
| Norbloc | 2-(2'-hydroxy-5-methacrylyloxyethylphenyl)-2H-benzotriazole |
| CGI 1850 | 1:1 (wgt) blend of 1-hydroxycyclohexyl phenyl ketone and bis(2,6-dimethoxybenzoyl)-2,4-4-trimethylpentyl phosphine oxide |
| PVP 2,500–40,000 | poly(N-vinyl pyrrolidone) having a molecular weight of approximately 2,500 to 40,000 |
| Blue HEMA | the reaction product of Reactive Blue 4 and HEMA, as described in Example 4 of U.S. Pat. No. 5,944,853 |
| IPA | isopropyl alcohol |
| D3O | 3,7-dimethyl-3-octanol |
| TEGDMA | tetraethyleneglycol dimethacrylate |
| TRIS | 3-methacryloxypropyltris(trimethylsiloxy)silane |
| Tween 80 | CAS number 9005-656 |
| Polyoxide (100,000–5,000,000) | poly(ethylene)oxide having a molecular weight of 100,000 to 5,000,000 |
| Tyloxapol | CAS number 25301-02-4 |
| DOE-120 | CTFA name: Polyethylene glycol 120 methyl glucose dioleate |
| EDTA | ethylenediamine tetraacetic acid |
| F127 | Poloxamer 407 NF, CAS number 106392-12-5 |
| DI | Deionized water |
| CYST | N,N'-bis(acryloyl)cystamine |

-continued

| | |
|---|---|
| Macromer 2 | the reaction product of described in the examples of U.S. pat. app. Ser. No. 10/028,400 filed on Dec. 20, 2001 and entitled Antimicrobial Contact Lenses and Methods for Their Production |
| DPMA | dipropylene glycol methyl ether acetate |
| N/A | not tested |
| Big Blue | A mixture of 900 mg blue HEMA, 44.1 g HEMA, 615 mg CGI 1850 and 150 mL ethylene glycol was stirred until homogeneous and the system was degassed as described in example 1. The mixture was transferred to a large crystallizing dish and covered with a watch glass. Polymerization of the olefinic moieties was conducted under visible light for approximately 1 hour (Phillips TL20 W/03T bulbs). Upon quenching of the polymerization using oxygen, the mixture was poured into 500 mL of borate- buffered saline solution and stirred for several hours until the material was transformed into a more rigid form. The liquids were decanted, and the product was washed with another 500 mL of borate-buffered saline solution, the polymer was cut into several smaller pieces, and stirred in 500 mL of deionized water for more than 1 hour to the point that the product became gel-like and sparingly soluble in the solvent. The mixture was then diluted with a small quantity of borate-buffered saline solution to enable better precipitation of the polymer. The mixture was filtered and washed in deionized water until the material did not appear soluble. The suspension was filtered, dried in a rotary evaporator, cut into smaller pieces and further dried until it appeared crystalline and anhydrous. The dark blue polymer was then milled into fine particles and subjected to more deionized water washings accompanied by 1 to 2 hours of stirring with each wash. Washing continued until little or no blue color was visible in solution and the product was filtered, dried at reduced pressure, and ground in a blender. GPC data for each of the polymers were obtained using both R.I and light scattering detectors. Chromatography was performed using a mixed bed GPC column (phenogel 300 mm × 7.8 mm × 5 micron (2) column (Phenomenex) having a separation range of 100 K to 10,000 K, and 0.5 wt % lithium bromide in dimethylformamide as the eluent. $Mn = 1.133 \times 10^6$; $Mw = 1.222 \times 10^6$; $Mz = 1.354 \times 10^6$; polydispersity $(Mw/Mn) = 1.078$. |

Lens Preparation

Lenses A

Monomer mix is prepared by blending 18.16 weight percent of GTP(Macromer 2), 28.29% mPDMS, 14.14% TRIS, 26.27% DMA, 5.05% HEMA, 5.05% PVP (360,000 molecular weight), 2.02% Norbloc, 0.02% Blue HEMA, 1% CGI 1850, in a blend with 79.84 parts of this combination with 20.16 parts D3O diluent and CYST 0.4%. Contact lenses were made by placing this monomer mix into thermoplastic contact lens molds, and irradiating using Philips TL20W/03T fluorescent bulbs at 70° C. for about 15 minutes. The molds were opened and lenses were extracted into DPMA solvent. The lenses were then rinsed in a 100 ppm Tween 80 in DI mixture to insure removal of solvent. The lenses were then equlibrated in deionized water.

Lenses B

Monomer mix is prepared by blending 17.98 weight percent of GTP(Macromer 2), 28% mPDMS, 14% TRIS, 26% DMA, 5% HEMA, 5% PVP, 2% Norbloc, 1% TEGDMA, 0.02% Blue HEMA,1% CGI 1850, in a blend with 80 parts of this combination with 20 parts D3O diluent and CYST 0.2%. Lenses were made in the same manner as Lenses A with the exception that lenses were extracted in IPA. Lenses were then placed into deionized water for equilibration.

Lenses C

Monomer mix is prepared by blending 17.98 weight percent of GTP(Macromer 2), 28% mPDMS, 14% TRIS, 26% DMA, 5% HEMA, 5% PVP, 2% Norbloc, 1% TEGDMA, 0.02% Blue HEMA, 1% CGI 1850, in a blend with 80 parts of this combination with 20 parts D3O diluent. Lenses were made in the same manner as Lenses A.

Lenses D

Monomer mix is prepared by blending 17.98 weight percent of GTP(Macromer 2), 28% mPDMS, 14% TRIS, 26% DMA, 5% HEMA, 5% PVP (360,000 molecular weight), 2% Norbloc, 1% TEGDMA, 0.02% Blue HEMA, 1% CGI 1850, in a blend with 80 parts of this combination with 20 parts D3O diluent. Lenses were made in the same manner as Lenses A, with the exception that the lens molds had a pHEMA(big blue) coating on the surface as per the method disclosed in U.S. patent application Ser. No. 09/921,192 entitled "Method for Correcting Articles by Mold Transfer," and that they were equilibrated into packing solution.

Lenses E

Monomer mix is prepared by blending 18.16 weight percent of GTP(Macromer 2), 28.29% mPDMS, 14.14% TRIS, 26.27% DMA, 5.05% HEMA, 5.05% PVP (360,000 molecular weight), 2.02% Norbloc, 0.02% Blue HEMA,1% CGI 1850, in a blend with 79.84 parts of this combination with 20.16 parts D3O diluent and CYST 0.4 Lenses were made in the same manner as Lenses A, with the exception that the lens molds had a pHEMA (big Blue) coating on the surface.

Lenses F
Lenses A were placed in a 10% silver nitrate solution for 60 minutes at room temperature for silver treatment. The lenses were then washed 3 times with DI water in 20 minute intervals to remove any excess silver. The lenses were then equilibrated in borate buffered saline.

Lenses G
Lenses B were placed in a 10% silver nitrate solution for 60 minutes at room temperature for silver treatment. The lenses were then washed 3 times with DI water in 20 minute intervals to remove any excess silver. The lenses were then equilibrated in borate buffered saline.

Lenses H
Lenses E were placed in a 10% silver nitrate solution for 60 minutes at room temperature for silver treatment. The lenses were then washed 3 times with DI water in 20 minute intervals to remove any excess silver. The lenses were then equilibrated in borate buffered saline.

Solution A
Solution A was made by adding 0.10 weight % of sodium borate, 0.91 weight % Boric Acid, 0.83% Sodium Chloride, 0.01% EDTA and 98.15 weight % water into a volumetric flask and was mixed at ambient temperature until all solids were dissolved. Solution A has a pH of 7.6 (measured at 20–30° C.), an osmolality of 170 (measured at ca. 25° C.) and a conductivity (m/S/cm) of 0.7 (measured at 20–30° C.)

Solution B
A solution was made by adding 0.185 weight % of sodium borate, 0.926 weight % Boric Acid and 98.89 weight % water into a volumetric flask and was mixed at ambient temperature until all solids were dissolved. Solution B has a pH of 7.0–7.6 (measured at 20–30° C.), an osmolality of 420 (measured at ca. 25° C.) and a conductivity (m/S/cm) of 14.5–15.5 (measured at 20–30° C.).

Solution C
Pure Vision Packing Solution removed from packaged commercially available Pure Vision Lenses.

Example 1

Solution A with a Variety of Surfactants

Lenses were added to individual polypropylene blister packs containing 950 µL of Solution A, and then the blister pack was heat sealed. Lenses were visually evaluated for lens' adhesion to the package, both prior to and after one autoclave cycle of 30 minutes±5 minutes at 121° C.±5° C. and subsequent cooling to room temperature. Different amounts of surfactants were added to Solution A and lenses were evaluated before and after an autoclave cycle to determine the degree of adhesion to a package. Solution B and Solution C (without any added surfactants) were evaluated as well. The data is presented below in Table 1 and Table 2

TABLE 1

| Solution A (except as noted) Solutions / Concentration (ppm) | Autoclaved | | | | |
|---|---|---|---|---|---|
| | Lenses D | Lenses A | Lenses G | Lenses H | Lenses E |
| No Surfactant | Stick | Stick | Stick | Stick | Stick |
| PVP (2,500) | | | | | |
| 50 | Stick | Stick | Stick | N/A | Mild Sticking |
| 100 | Stick | Stick | Stick | N/A | Stick |
| 250 | Stick | Stick | Stick | Stick | Stick |
| PVP (10,000) | | | | | |
| 50 | Stick | Stick | Stick | N/A | Stick |
| 100 | Stick | Stick | Stick | N/A | Stick |
| 250 | Stick | Stick | Stick | Stick | Stick |
| 1000 | No Sticking | Stick | Stick | N/A | Stick |
| Polyoxide (100,000) | | | | | |
| 50 | Stick | Stick | N/A | N/A | Stick |
| 100 | Stick | Stick | N/A | N/A | Stick |
| 250 | Stick | Mild Sticking | Stick | Stick | Stick |
| Tween 80 | | | | | |
| 50 | Stick | N/A | N/A | N/A | N/A |
| 100 | Stick | N/A | N/A | N/A | N/A |
| 250 | Stick | Mild Sticking | Stick | Mild Sticking | Stick |
| PVP (25,000) | | | | | |
| 1000 | Stick | Stick | Stick | Stick | Stick |
| PVP (40,000) | | | | | |
| 1000 | Stick | Stick | Stick | Stick | Stick |
| F127 | | | | | |
| 1000 | No Sticking | No Sticking | No Sticking | No Sticking | No Sticking |
| Solution B. | Stick | Stick | Stick | Stick | Stick |
| Solution C | Stick | N/A | N/A | N/A | N/A |

TABLE 1-continued

| Solution A (except as noted) Solutions / Concentration | Autoclaved | | | | |
|---|---|---|---|---|---|
| (ppm) | Lenses D | Lenses A | Lenses G | Lenses H | Lenses E |
| Tyloxapol | | | | | |
| 10,000 | Stick | N/A | N/A | N/A | N/A |
| Polyoxide (300,000) | | | | | |
| 10,000 | Stick | N/A | N/A | N/A | N/A |
| Polyoxide (5,000,000) | | | | | |
| 1000 | Stick | N/A | N/A | N/A | N/A |

TABLE 2

| Solution A (except as noted) Solutions/ Concentration | Non-Autoclaved | | | | |
|---|---|---|---|---|---|
| (ppm) | Lenses D | Lenses A | Lenses G | Lenses H | Lenses E |
| No Surfactant | Stick | Stick | Stick | Stick | Stick |
| PVP (2,500) | | | | | |
| 50 | Stick | Stick | Stick | N/A | Mild Sticking |
| 100 | Stick | Stick | Stick | N/A | Stick |
| 250 | Mild Sticking | Mild Sticking | Mild Sticking | Stick | Mild Sticking |
| PVP (10,000) | | | | | |
| 50 | Stick | Stick | Stick | N/A | Stick |
| 100 | Stick | Stick | Mild Sticking | N/A | Mild Sticking |
| 250 | Mild Sticking | Mild Sticking | Mild Sticking | Mild Stick | Stick |
| 1000 | No Sticking | Stick | Stick | N/A | Stick |
| Polyoxide (100,000) | | | | | |
| 50 | Stick | Stick | N/A | N/A | Mild Sticking |
| 100 | Stick | Stick | N/A | N/A | Stick |
| 250 | Mild Sticking | Mild Sticking | Mild Sticking | No Sticking | Stick |
| Tween 80 | | | | | |
| 50 | Mild Sticking | N/A | N/A | N/A | N/A |
| 100 | No Sticking | N/A | N/A | N/A | N/A |
| 250 | Mild Sticking | No Sticking | No Sticking | N/A | Mild Sticking |
| PVP (25,000) | | | | | |
| 1000 | No Sticking | Stick | No Sticking | N/A | Stick |
| PVP (40,000) | | | | | |
| 1000 | Stick | Stick | No Sticking | N/A | Stick |
| F127 | | | | | |
| 1000 | No Sticking | No Sticking | No Sticking | No Sticking | No Sticking |
| Solution B. | Stick | Stick | Stick | Stick | Stick |
| Solution C | Stick | N/A | N/A | N/A | N/A |
| Tyloxapol | | | | | |
| 1% | No Sticking | N/A | N/A | N/A | N/A |
| Polyoxide (300,000) | | | | | |
| 1% | No Sticking | N/A | N/A | N/A | N/A |
| Polyoxide (5,000,000) | | | | | |
| 1000 ppm | No Sticking | N/A | N/A | N/A | N/A |

Example 2

Solution A with a Variety of Surfactants

Lenses were added to individual polypropylene blister packs and subsequently 950 μL of Solution A, was added to the blister packs. The filled packs were heat sealed. Lenses were visually evaluated for lens' adhesion to the package, both prior to and after one autoclave cycle of 30 minutes±5 minutes at 121° C.±5° C. and subsequent cooling to room temperature. Different amounts of surfactants were added to Solution A and lenses were evaluated before and after an autoclave cycle to determine the degree of adhesion to a package. Solution B and Solution C (without any added surfactants) were evaluated as well. The data is presented below in Table 3 and Table 4.

TABLE 3

| Lens First Solutions / Concentration (ppm) | Autoclaved | | | | |
|---|---|---|---|---|---|
| | Lenses D | Lenses A | Lenses G | Lenses H | Lenses E |
| No Surfactant | Stick | Stick | Stick | Stick | Stick |
| PVP (2,500) | | | | | |
| 50 | Stick | Stick | Stick | N/A | Stick |
| 100 | Stick | Stick | Stick | N/A | Stick |
| 250 | Stick | Stick | Stick | Stick | Stick |
| PVP (10,000) | | | | | |
| 50 | Stick | Stick | Stick | N/A | Stick |
| 100 | Stick | Stick | Stick | N/A | Stick |
| 250 | Stick | Stick | Stick | Stick | Stick |
| 1000 | N/A | N/A | Stick | Stick | Stick |
| Polyoxide (100,000) | | | | | |
| 50 | Stick | Stick | N/A | N/A | Stick |
| 100 | Stick | Stick | N/A | N/A | Stick |
| 250 | Stick | Mild Sticking | Stick | Stick | Stick |
| Tween 80 | | | | | |
| 50 | Stick | N/A | N/A | N/A | N/A |
| 100 | Stick | N/A | N/A | N/A | N/A |
| 250 | Stick | Mild Sticking | Mild Sticking | No Sticking | Stick |
| PVP (25,000) | | | | | |
| 1000 | Stick | Stick | Stick | N/A | N/A |
| PVP (40,000) | | | | | |
| 1000 | Stick | Stick | No Sticking | Stick | N/A |
| F127 | | | | | |
| 1000 | N/A | N/A | N/A | N/A | N/A |
| Solution B | Stick | Stick | Stick | Stick | Stick |
| Solution C | N/A | N/A | N/A | N/A | N/A |
| Tyloxapol | | | | | |
| 10,000 | No Sticking | N/A | N/A | N/A | N/A |
| Polyoxide (300,000) | | | | | |
| 10,000 | No Sticking | N/A | N/A | N/A | N/A |
| Polyoxide (5,000,000) | | | | | |
| 1000 | No Sticking | N/A | N/A | N/A | N/A |

TABLE 4

| Lens First (A) Solutions / Concentration (ppm) | Non-Autoclaved | | | | |
|---|---|---|---|---|---|
| | Lenses D | Lenses A | Lenses H | Lenses I | Lenses E |
| No Surfactant | Stick | Stick | Stick | Stick | Stick |
| PVP (2,500) | | | | | |
| 50 | Stick | Stick | Stick | N/A | Mild Sticking |
| 100 | Stick | Stick | Stick | N/A | Stick |
| 250 | Mild Sticking | Mild Sticking | Stick | Stick | Stick |

TABLE 4-continued

| Lens First (A) Solutions / Concentration (ppm) | Non-Autoclaved | | | | |
|---|---|---|---|---|---|
| | Lenses D | Lenses A | Lenses H | Lenses I | Lenses E |
| PVP (10,000) | | | | | |
| 50 | Stick | Stick | Stick | N/A | Stick |
| 100 | Stick | Stick | Stick | N/A | Stick |
| 250 | Mild Sticking | Mild Sticking | Stick | Stick | Stick |
| 1000 | Mild Sticking | Stick | No Sticking | N/A | Stick |
| Polyoxide (100,000) | | | | | |
| 50 | Stick | Stick | N/A | N/A | Stick |
| 100 | Stick | Stick | N/A | N/A | Stick |
| 250 | Mild Sticking | Mild Sticking | No Sticking | Stick | Mild Sticking |
| Tween 80 | | | | | |
| 50 | Mild Sticking | No Sticking | N/A | N/A | N/A |
| 100 | Stick | N/A | N/A | N/A | N/A |
| 250 | Mild Sticking | N/A | No Sticking | N/A | No Sticking |
| PVP (25,000) | | | | | |
| 1000 | Stick | Stick | No Sticking | N/A | Mild Sticking |
| PVP (40,000) | | | | | |
| 1000 | Stick | Stick | Mild Sticking | N/A | Mild Sticking |
| F127 | | | | | |
| 1000 | N/A | N/A | N/A | N/A | N/A |
| Solution B | Stick | Stick | Stick | Stick | Stick |
| Solution C | N/A | N/A | N/A | N/A | N/A |
| Tyloxapol | | | | | |
| 1% | No Sticking | N/A | N/A | N/A | N/A |
| Polyoxide (300,000) | | | | | |
| 1% | No Sticking | N/A | N/A | N/A | N/A |
| Polyoxide (5,000,000) | | | | | |
| 1000 ppm | No Sticking | N/A | N/A | N/A | N/A |

Example 3

Solution A with a Variety of Surfactants

Lenses were added to individual polypropylene blister packs containing 1.0 mL of Solution A, was added to the blister packs. The filled packs were heat sealed. Lenses were visually evaluated for lens' adhesion to the package, both prior to and after one autoclave cycle of 30 minutes±5 minutes at 121° C.±5° C. and subsequent cooling to room temperature. Different amounts of surfactants were added to Solution A and lenses were evaluated before and after an autoclave cycle to determine the degree of adhesion to a package. The results were the same before and after autoclave and the data is presented below in Table 5.

TABLE 5

| Lenses | Solution/ concentration ppm | Total # lenses | 1 | 2 | 3 | 4 |
|---|---|---|---|---|---|---|
| Lenses C | No Surfactant | 6 | | | | 6 |
| Lenses C | PVP 360,000/1000 | 6 | | 6 | | |
| Lenses C | PEO 5,000,000/1000 | 6 | | 6 | | |
| Lenses C | DOE-120/1000 | 6 | 6 | | | |
| Lenses D | No surfactant | 5 | | | | 5 |
| Lenses D | DOE-120/500 | 5 | 5 | | | |
| Lenses D | DOE-120/250 | 5 | | 3 | 2 | |
| Lenses D | DOE-120/100 | 5 | | 3 | 2 | |

1 = completely free floating with no adhesion when package is rotated.
2 = may not initially be free floating, but becomes so with minimal agitation (shaking or tapping).
3 = partial lens' adhesion to package (one or more contact points). The remainder of the lens will move with minimal agitation, but the total lens is not free floating.
4 = complete adhesion to the package with no movement.

What is claimed is:

1. A method of inhibiting the adherence of soft lenses to hydrophobic packaging materials comprising storing the soft lenses in a packing solution comprising an effective amount of composition of Formula I

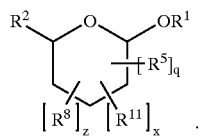

wherein
$R^1$ is $C_{1-6}$alkyl;
$R^2$ is —$CH_2OH$, —$CH_2OR^3$, —$CH_2OC(O)R^4$
 wherein $R^3$ is $C_{1-50}$alkyl, or $C_{1-51}$alkylene having at least one double bond, $R^4$ is hydrogen or $C_{1-12}$alkyl;
$R^5$ is —OH, or —[(O—(CHR$^7$)$_a$)$_n$—OR$^6$]
 wherein $R^6$ is hydrogen $C_{1-50}$alkyl, or $C_{1-51}$alkylene having at least one double bond, $R^7$ is hydrogen or $C_{1-12}$alkyl;
$R^8$ is —OH or —[(O—(CHR$^{10}$)$_b$)$_m$—OR$^9$]
 wherein $R^9$ is hydrogen, $C_{1-50}$alkyl, or $C_{1-51}$alkylene having at least one double bond $R^{10}$ is hydrogen or $C_{1-12}$alkyl;
$R^{11}$ is —OH or —OC(O)$R^{12}$
 wherein $R^{12}$ is $C_{1-50}$alkyl or $C_{1-51}$alkylene having at least one double bond;
a is 2–4;
b is 2–4;
x is 0–3;
q is 0–3;
z is 0–3
 wherein the sum of x+q+z=3
m is an integer, from 1 to 200;
n is an integer from 1 to 200 wherein the sum of m+n=2 to 400
 provided that if q is 3 $R^6$ is not ethyl;
 provided that if z is 3 $R^9$ is not ethyl.

2. The method of claim 1 wherein
$R^1$ is methyl, ethyl or propyl,
$R^2$ is —$CH_2)C(O)R^4$,
$R^4$ is $C_{8-30}$alkyl, or $C_{10-30}$alkylene having at least one double bond,
$R^5$ is —[(O—(CHR$^7$)$_a$)$_n$—OR$^6$],
$R^6$ is $C_{8-30}$alkyl, or $C_{10-30}$alkylene having at least one double bond,
$R^7$ is hydrogen,
$R^8$ is —[(O—(CHR$^{10}$)$_b$)$_m$—OR$^9$]
$R^9$ is $C_{8-30}$alkyl, or $C_{10-30}$alkylene having at least one double bond,
$R^{10}$ is hydrogen,
$R^{11}$ is OC(O)$R^{12}$
$R^{12}$ is $C_{8-30}$alkyl or $C_{10-30}$alkylene having at least one double bond,
a is 2–3,
b is 2–3,
x is 1,
q is 1,
z is 1,
m is 60–140
n is 80–120,
wherein the sum of m+n is about 100 to about 200.

3. The method of claim 1 wherein
$R^1$ is methyl or ethyl,
$R^2$ is —$CH_2OC(O)R^4$,
$R^4$ is $C_{14-22}$alkyl, or $C_{14-22}$alkylene having at least one double bond,
$R^5$ is —[(O—(CHR$^7$)$_a$)$_n$—OR$^6$],
$R^6$ is $C_{14-22}$alkyl, or $C_{14-22}$alkylene having at least one double bond,
$R^7$ is hydrogen,
$R^8$ is —[(O—(CHR$^{10}$)$_b$)$_m$—OR$^9$]
$R^9$ is $C_{14-22}$alkyl, or $C_{14-22}$alkylene having at least one double bond,
$R^{10}$ is hydrogen,
$R^{11}$ is OC(O)$R^{12}$,
$R^{12}$ is $C_{14-22}$alkyl, or $C_{14-22}$alkylene having at least one double bond,
a is 2–3,
b is 2–3,
x is 1,
q is 1,
z is 1,
m is 60–140
n is 80–120,
wherein the sum of m+n is about 100 to about 200.

4. The method of claim 1 wherein
$R^1$ is methyl or ethyl,
$R^2$ is —$CH_2OC(O)R^4$,
$R^4$ is $C_{16-20}$alkyl, or $C_{16-20}$alkylene having at least one double bond,
$R^5$ is —[(O—(CHR$^7$)$_a$)$_n$—OR$^6$],
$R^6$ is $C_{16-20}$alkyl, or $C_{16-20}$alkylene having at least one double bond,
$R^7$ is hydrogen,
$R^8$ is —[(O—(CHR$^{10}$)$_b$)$_m$—OR$^9$]
$R^9$ is $C_{16-20}$alkyl, or $C_{16-20}$alkylene having at least one double bond,
$R^{10}$ is hydrogen,
$R^{11}$ is OC(O)$R^{12}$,
$R^{12}$ is $C_{16-20}$alkyl, or $C_{16-20}$alkylene having at least one double bond,
a is 2–3,
b is 2–3,
x is 1,
q is 1,
z is 1,
m is 60–140
n is 80–120,
wherein the sum of m+n is about 100 to about 200.

5. The method of claim 1 wherein the compound of Formula I is poly(oxy-1,2-ethandiyl) α-hydro-ω-hydroxy-, ether with methyl D-glucopyranoside 2,6-di-9Z-9-octadecenaoate.

6. The method of claim 1 wherein the effective amount of a compound of Formula I is about 0.01 weight percent to about 2.0 weight percent.

7. The method of claim 1 wherein the effective amount of a compound of Formula I is about 0.05 weight percent to about 1.5 weight percent.

8. The method of claim 1 wherein the effective amount of a compound of Formula I is about 0.05 weight percent to about 0.1 weight percent.

9. The method of claim 1 wherein the compound of Formula I is poly(oxy-1,2-ethandiyl) α-hydro-ω-hydroxy-, ether with methyl D-glucopyranoside 2,6-di-9Z-9-octadecenaoate and the effective amount is about 0.01 weight percent to about 2.0 weight percent.

10. The method of claim 1 wherein the compound of Formula I is poly(oxy-1,2-ethandiyl) α-hydro-ω-hydroxy-, ether with methyl D-glucopyranoside 2,6-di-9Z-9-octadecenaoate and the effective amount is about 0.035 weight percent to about 0.075 weight percent.

11. The method of claim 1 wherein the soft contact lens is a silicone hydrogel.

12. The method of claim 1 wherein the soft contact lens is selected from the groups consisting of acquafilcon A, balafilcon A, and lotrafilcon A.

13. A soft contact lens that is stored in a packing solution comprising an effective amount of composition of Formula I

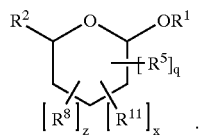

I wherein
$R^1$ is $C_{1-6}$alkyl;
$R^2$ is —$CH_2OH$, —$CH_2OR^3$, —$CH_2OC(O)R^4$
  wherein $R^3$ is $C_{1-50}$alkyl, or $C_{1-51}$alkylene having at least one double bond, $R^4$ is hydrogen or $C_{1-12}$alkyl;
$R^5$ is —OH, or —$[(O-(CHR^7)_a)_n-OR^6]$
  wherein $R^6$ is hydrogen $C_{1-50}$alkyl, or $C_{1-51}$alkylene having at least one double bond, $R^7$ is hydrogen or $C_{1-12}$alkyl;
$R^8$ is —OH or —$[(O-(CHR^{10})_b)_m-OR^9]$
  wherein $R^9$ is hydrogen, $C_{1-50}$alkyl, or $C_{1-51}$alkylene having at least one double bond $R^{10}$ is hydrogen or $C_{1-12}$alkyl;
$R^{11}$ is —OH or —$OC(O)R^{12}$
  wherein $R^{12}$ is $C_{1-50}$alkyl or $C_{1-51}$alkylene having at least one double bond;
a is 2–4;
b is 2–4;
x is 0–3;
q is 0–3;
z is 0–3
  wherein the sum of x+q+z=3
m is an integer, from 1 to 200;
n is an integer from 1 to 200 wherein the sum of m+n=2 to 400
  provided that if q is 3 $R^6$ is not ethyl;
  provided that if z is 3 $R^9$ is not ethyl.

14. The lens of claim 13 wherein
$R^1$ is methyl, ethyl or propyl,
$R^2$ is —$CH_2OC(O)R^4$,
$R^4$ is $C_{8-30}$alkyl, or $C_{10-30}$alkylene having at least one double bond,
$R^5$ is —$[(O-(CHR^7)_a)_n-OR^6]$,
$R^6$ is $C_{8-30}$alkyl, or $C_{10-30}$alkylene having at least one double bond,
$R^7$ is hydrogen,
$R^8$ is —$[(O-(CHR^{10})_b)_m-OR^9]$
$R^9$ is $C_{8-30}$alkyl, or $C_{10-30}$alkylene having at least one double bond,
$R^{10}$ is hydrogen,
$R^{11}$ is $OC(O)R^{12}$,
$R^{12}$ is $C_{8-30}$alkyl or $C_{10-30}$alkylene having at least one double bond,
a is 2–3,
b is 2–3,
x is 1,
q is 1,
z is 1,
m is 60–140
n is 80–120,
wherein the sum of m+n is about 100 to about 200.

15. The lens of claim 13 wherein
$R^1$ is methyl or ethyl,
$R^2$ is —$CH_2OC(O)R^4$,
$R^4$ is $C_{14-22}$alkyl, or $C_{14-22}$alkylene having at least one double bond,
$R^5$ is —$[(O-(CHR^7)_a)_n-OR^6]$,
$R^6$ is $C_{14-22}$alkyl, or $C_{14-22}$alkylene having at least one double bond,
$R^7$ is hydrogen,
$R^8$ is —$[(O-(CHR^{10})_b)_m-OR^9]$
$R^9$ is $C_{14-22}$alkyl, or $C_{14-22}$alkylene having at least one double bond,
$R^{10}$ is hydrogen,
$R^{11}$ is $OC(O)R^{12}$,
$R^{12}$ is $C_{14-22}$alkyl, or $C_{14-22}$alkylene having at least one double bond,
a is 2–3,
b is 2–3,
x is 1,
q is 1,
z is 1,
m is 60–140
n is 80–120,
wherein the sum of m+n is about 100 to about 200.

16. The lens of claim 13 wherein
$R^1$ is methyl or ethyl,
$R^2$ is —$CH_2OC(O)R^4$,
$R^4$ is $C_{16-20}$alkyl, or $C_{16-20}$alkylene having at least one double bond,
$R^5$ is —$[(O-(CHR^7)_a)_n-OR^6]$,
$R^6$ is $C_{16-20}$alkyl, or $C_{16-20}$alkylene having at least one double bond,
$R^7$ is hydrogen,
$R^8$ is —$[(O-(CHR^{10})_b)_m-OR^9]$
$R^9$ is $C_{16-20}$alkyl, or $C_{16-20}$alkylene having at least one double bond,
$R^{10}$ is hydrogen,
$R^{11}$ is $OC(O)R^{12}$,
$R^{12}$ is $C_{16-20}$alkyl, or $C_{16-20}$alkylene having at least one double bond,
a is 2–3,
b is 2–3,
x is 1,
q is 1,
z is 1, m is 60–140 n is 80–120, wherein the sum of m+n is about 100 to about 200.

17. The lens of claim 13 wherein the compound of Formula I is poly(oxy-1,2-ethandiyl) α-hydro-ω-hydroxy-, ether with methyl D-glucopyranoside 2,6-di-9Z-9-octadecenaoate.

18. The lens of claim 13 wherein the effective amount of a compound of Formula I is about 0.01 weight percent to about 2.0 weight percent.

19. The lens of claim 13 wherein the effective amount of a compound of Formula I is about 0.05 weight percent to about 1.5 weight percent.

20. The lens of claim 13 wherein the effective amount of a compound of Formula I is about 0.05 weight percent to about 0.1 weight percent.

21. The lens of claim 13 wherein the compound of Formula I is poly(oxy-1,2-ethandiyl) α-hydro-ω-hydroxy-, ether with methyl D-glucopyranoside 2,6-di-9Z-9-octadecenaoate and the effective amount is about 0.01 weight percent to about 2.0 weight percent.

22. The lens of claim 13 wherein the compound of Formula I is poly(oxy-1,2-ethandiyl) α-hydro-ω-hydroxy-, ether with methyl D-glucopyranoside 2,6-di-9Z-9-octadecenaoate and the effective amount is about 0.035 weight percent to about 0.075 weight percent.

23. The lens of claim 13 wherein the soft contact lens is a silicone hydrogel.

24. The lens of claim 13 wherein the soft contact lens is selected from the groups consisting of acquafilcon A, balafilcon A, and lotrafilcon A.

* * * * *